United States Patent [19]

Ikeda

[11] Patent Number: 4,698,308

[45] Date of Patent: Oct. 6, 1987

[54] DEVICE FOR MEASURING THE NUMBER OF BACTERIA IN SUPERPURE WATER

[75] Inventor: Mitsuru Ikeda, Kanagawa, Japan

[73] Assignee: Fuji Photo Film Co., Ltd., Kanagawa, Japan

[21] Appl. No.: 829,387

[22] Filed: Feb. 14, 1986

[30] Foreign Application Priority Data

Feb. 14, 1985 [JP] Japan .................................. 60-26706

[51] Int. Cl.$^4$ ............................................. C12M 1/34
[52] U.S. Cl. .................................... 435/291; 435/287;
435/808; 250/361 R; 250/364
[58] Field of Search .............. 435/808, 317, 291, 287;
250/361 R, 361 C, 362, 363, 364, 356.1, 357.1

[56] References Cited

U.S. PATENT DOCUMENTS

| 3,912,929 | 10/1975 | Cobb et al. | 250/364 X |
|---|---|---|---|
| 3,916,197 | 10/1975 | Fulwyler | 250/361 |
| 4,283,490 | 8/1981 | Plakas | 435/291 X |
| 4,467,032 | 8/1984 | Lowke et al. | 435/291 X |
| 4,563,331 | 1/1986 | Losee et al. | 250/361 C X |
| 4,603,256 | 7/1986 | Lelong | 250/361 R |

Primary Examiner—Larry Jones
Attorney, Agent, or Firm—Sughrue, Mion, Zinn, Macpeak and Seas

[57] ABSTRACT

A device for continuously and accurately measuring the number of bacteria present in superpure water such as may be used in the manufacture of semiconductor devices and the like. A sample flow of the superpure water is passed through a generally rectangular measuring flow path having a small thickness and large width. A reagent is added to the flow in the measuring flow path of a type which reacts with bacteria to produce products which fluoresce upon application of an exciting light beam. The light produced by such fluorescence is detected and the detection output converted to a signal indicative of the number of bacteria present in the sample flow.

8 Claims, 3 Drawing Figures

DEVICE FOR MEASURING THE NUMBER OF BACTERIA IN SUPERPURE WATER

BACKGROUND OF THE INVENTION

The present invention relates to a device for measuring the number of bacteria in superpure water, and more particularly to a device for measuring the number of bacteria in superpure water used for manufacturing semiconductor devices or the like.

In water quality inspection, it is essential to detect both the types of bacteria in the water under test and how many bacteria are included in a given unit quantity of the water. Detection of the number of bacteria in water is absolutely necessary for superpure water such as is required in manufacturing medicines in which the number of bacteria must be limited to an extremely small value, or in the case of manufacturing semiconductor devices (especially super-LSI semiconductor devices) in which the number of bacteria per 10 cc of superpure water is limited to ten or less.

In a conventional method of detecting the number of bacteria in a unit quantity of superpure water, a sample of the water is extracted and the bacteria in the sample are cultivated to allow them to multiply. The bacteria thus treated are filtered and stained, and the stained bacteria are counted under a microscope.

When such a detecting method is employed, it takes about seven days to accomplish all of the steps from sampling the superpure water to counting the number of bacteria. If the quality of the superpure water is thereby determined unacceptable, the semiconductor devices manufactured during the detection period must be discarded, which increases the average manufacturing cost of the devices.

The present inventors have proposed a bacteria counter which can detect the number of bacteria in water under test in an extremely short period of time, with the result that the manufacturing cost of semiconductor devices or the like can be reduced.

The bacteria counter proposed by the present inventors fundamentally is composed of a transparent measurement chamber into which the water under test is introduced and to which acridine orange or a derivative thereof is added to react with the bacteria contained in the water under test to form reaction products, an exciting light source for applying an exciting light beam to the water under test in the measurement chamber to cause the reaction products to fluoresce, a photoelectric converter for detecting the amount of fluorescent light so produced, and an arithmetic unit for converting the output of the photoelectric converter to the corresponding number of bacteria per unit quantity of water.

The present inventors have found that, where fluorescein diacetate, ethidium bromide, or ethidium iodide, is used as the reagent added to the water under test to react with the bacteria in the water to form reaction products which fluoresce when an exciting light beam is applied, the reagent reacted with the bacteria produces fluorescence, but not the free reagent in the pure water.

SUMMARY OF THE INVENTION

An object of the invention is to provide a device for continuously measuring the number of bacteria in superpure water with which the number of bacteria in superpure water with which the number of bacteria in the water under test can be detected in an extremely short time, and hence with the use of which the manufacturing cost of semiconductor devices or the like can be reduced.

Another object of the invention is to provide a device for measuring the number of bacteria in superpure water with which an extremely small number of bacteria in the water under test can be detected as required in the manufacture of semiconductor devices.

A further object of the invention is to provide a device for measuring the number of bacteria in superpure water which is high in reliability because it uses no movable member for application of an exciting light beam.

In order to achieve the foregoing objects of the invention, a device for measuring the number of bacteria in superpure water according to the invention comprises: means for delivering water under test to a measuring flow path to which a reagent has been added whereby products formed by reaction of the reagent with the bacteria fluoresce when an exciting light beam is applied, an exciting light source for applying the exciting light beam to the water under test in the measuring flow path to cause the reaction products to fluoresce, and a photoelectric converter for detecting the amount of fluorescent light so produced, wherein the measuring flow path is rectangular in section and has a small thickness in the direction of application of the exciting light beam and a large width perpendicular to the thickness direction, and the exciting light beam is applied linearly in the widthwise direction of the measuring flow path.

DESCRIPTION OF THE PREFERRED EMBODIMENTS

The invention will be described in detail with reference to the accompanying drawings.

Figure 1:
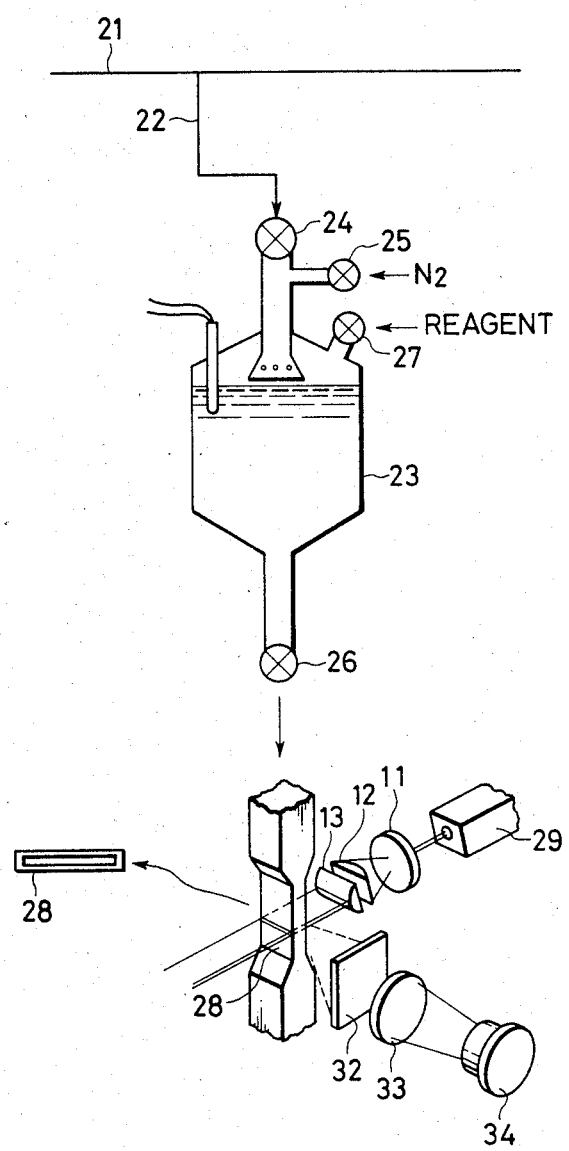
FIGS. 1 and 2 are a perspective view and a block diagram, respectively, of a preferred embodiment of a device for measuring a number of bacteria constructed according to the invention.

In FIG. 1, reference numeral 21 designates a line carrying superpure water extending, for instance, to a semiconductor manufacturing facility, and reference numeral 23 designates a reaction chamber in which a reaction is caused by adding a reagent to water under test supplied through a branch pipe 22. The reagent reacts with the DNA of the bacteria in water under test to form high-density reaction products in the bacteria. These products fluoresce relatively strongly when an exciting light beam is applied thereto. For instance, for an exciting light beam of wavelength of about 440 nm to 500 nm (such as an argon laser of 488 nm), the products fluoresce at about 500 nm to 580 nm with the peak value occurring at about 530 nm. The reagent is such that only products formed through the reaction of the reagent with the bacteria in the water fluoresce. The free reagent in the pure water does not fluoresce, even when the exciting light beam is applied. Examples of suitable reagents are fluorescein diacetate, ethidium bromide, and eithidium iodide.

The reagent is used by adding, for instance, 100 to 200 micrograms of reagent to 100 cc of the water under test (being added as 1 cc of acetone solution).

Further, $N_2$ gas is supplied into the reaction chamber 23. The $N_2$ gas is a pressurized gas used to inject the measurement water obtained by adding the reagent to the pure water into a measurement chamber 28. Further in FIG. 1, reference numerals 24, 25 and 26 respectively designate valves for the superpure water, the $N_2$ gas, and the measurement water. By adjusting these valves, the flow rate of the measurement water in the measurement chamber 28 can be controlled. A valve 27 is provided for adding the reagent.

The measurement water in which the reaction products are formed in the reaction chamber 23 is jetted into the measurement chamber 28 by the pressure of the $N_2$ gas. As shown in FIG. 1, the measurement chamber 28 has a flow path of rectangular section, the thickness of which is extremely small in the direction of application of the exciting light beam and the width of which is large. The thickness of the measurement chamber 28 is determined from the S/N ratio of a signal based on the volume of the irradiating part of the exciting light beam. The space is preferably rectangular in section, having typical dimensions of 100 to 200 microns by 10 mm. The measurement chamber 8 is used to apply the exciting light beam to the water under measurement in which the reaction products have been formed to cause the reaction to fluoresce and to permit the measurement of the intensity of the fluorescent light thus produced. For these purposes, at least a part of the measurement chamber 28 should be able to transmit light in the wavelength range of the exciting light and the product's output fluorescent light. Accordingly, the measurement chamber can be formed of a quartz tube, for instance.

Further in FIG. 1, reference numeral 29 designates an exciting light source such as an argon laser (488 nm). The exciting light source 29 applies an exciting light beam linearly to the water in the measurement chamber 28 through a concave lens 11 and two cylindrical lenses 12 and 13, the longitudinal axes of which are perpendicular to each other. The lenses 11, 12 and 13 are used to concentrate the exciting light beam into a linear beams of a width of 100 microns or less and to apply the concentrated exciting light beam to the measurement chamber, thereby to improve the measurement accuracy.

As shown in FIG. 1, a photomultiplier 34 receives the fluorescent light produced when the exciting light beam is applied to the water in the measurement chamber 28 and produces an output according to the intensity of that light. An interference filter 32 and a condensing optical system 33 are provided on the incident side of the photomultiplier 34. In order to prevent the generation of noise due to a portion of the exciting light beam reaching the photomultiplier directly, it is preferable that the photomultiplier be arranged perpendicular to the optical axis of the exciting light beam.

Figure 2:
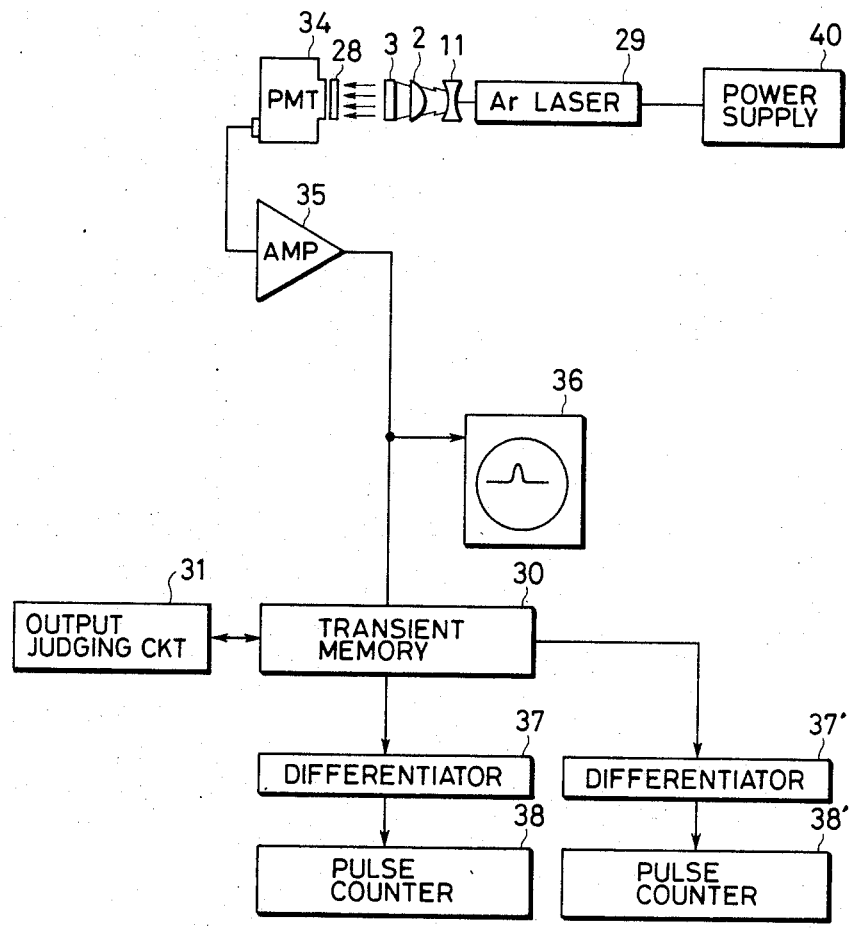

As shown in FIG. 2, the output of the photomultiplier 34 is amplified by an amplifier 35 and then applied to an oscilloscope 36 to thus provide an indication of the presence of the fluorescent light. The output of the amplifier 35 is also applied through differentiator circuits 37 and 37' to pulse counters 38 and 38', respectively, to directly count the number of bacteria. Further in FIG. 2, reference numeral 40 designates a power supply for the laser source 29. A transient memory 30 and an output determining circuit 31 are provided to respectively store the output of the amplifier 35 and to determine the magnitude of the output, thereby to determine whether the output is due to fluorescence of live or dead bacteria. That is, since the fluorescent output due to live bacteria is significantly higher than the dead bacteria, these outputs can be easily distinguished.

Figure 3:
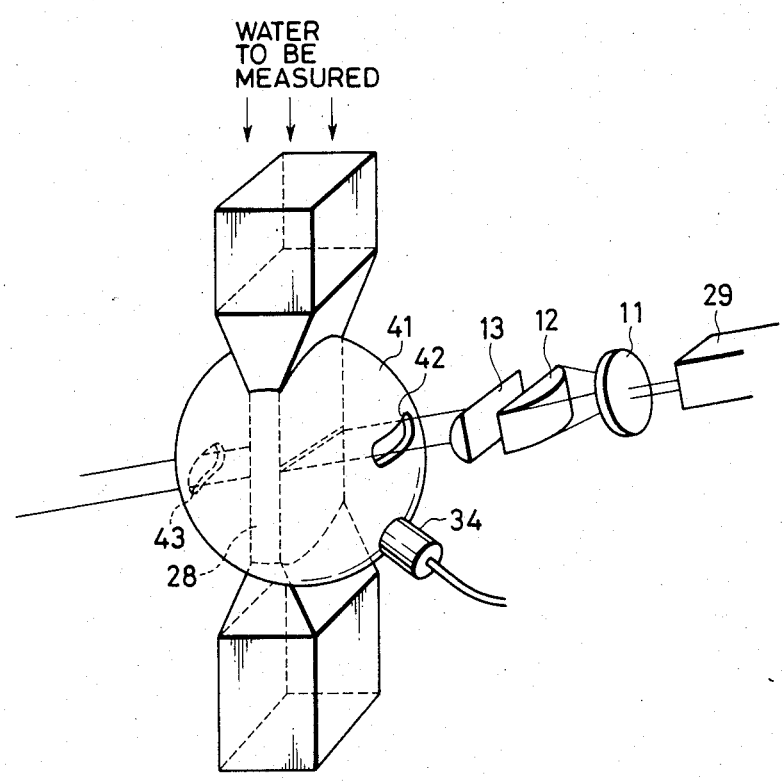
FIG. 3 is a perspective view showing essential components of another embodiment of the invention.

As shown in FIG. 3, a spherical mirror 41 is provided which surrounds the measurement chamber 28. The spherical mirror 41 is employed to apply to the photomultiplier 34 with a high efficiency the fluorescent light which is produced by applying the exciting light beam to the measurement water. The spherical mirror 41 has an opening 42 for incidence of the exciting light beam and an opening 43 for emergence of the exciting light beam. The photomultiplier 34 is mounted on the spherical mirror 41.

In the above-described embodiment, the number of bacteria in the entire water flow passing through the measurement chamber is detected. However, it is possible to detect the number of bacteria in only a part of the measurement water passing through the measurement chamber, and according to the number of bacteria thus detected, the number of bacteria in the entire the measurement water flow calculated.

Further, in the above-described embodiment, only the number of bacteria is detected. However, if the light reflected in the measurement water (having the same wavelength as the exciting light beam) is also measured, the quantity of impurities in the measurement water can also be detected. That is, in this case, both the number of bacteria and the quantity of impurities other than bacteria can be determined. To measure the light reflected in the measurement water, it is not always necessary to use the measurement chamber for detecting the number of bacteria; that is, the measurement may be carried out using two measurement chambers connected in series.

As is apparent from the above description, according to the invention, the number of bacteria in the measurement water can be accurately detected in an extremely short period of time. Therefore, the manufacturing cost of semiconductor devices or the like can be reduced. Since even an extremely small number of bacteria can be detected as required especially for the manufacture of semiconductor devices, the invention can greatly contribute to a reduction of the manufacturing cost of semiconductor devices.

I claim:

1. A device for measuring the number of bacteria in superpure water, comprising:
   means for conducting water under test including a measuring flow path;
   means for adding a reagent to the water in said measuring flow path of a type such that products formed by reaction of said reagent with bacteria fluoresce when exposed to an exciting light beam;
   an exciting light source for applying an exciting light beam to said water in said measuring flow path to cause said reaction products to fluoresce;
   a photoelectric converter receiving light produced when said products fluoresce;
   means for differentiating an output of said photoelectric converter; and
   means for counting an output of said differentiating means,
   said measuring flow path being rectangular in section and having a small thickness in a direction of application of said exciting light beam and a large width perpendicular to a direction of said thickness, said exciting light beam being linearly applied in a widthwise direction of said measuring flow path.

2. The device as claimed in claim 1, wherein said exciting light source comprises a laser source and a plurality of cylindrical lenses, said exciting light beam being applied linearly in said widthwise direction of said measuring flow path through said cylindrical lenses.

3. The device as claimed in claim 1, wherein said reagent comprises at least one reagent selected from the group consisting of fluorescein diacetate, ethidium bromide, and ethidium iodidie.

4. The device as claimed in claim 1, wherein said device further comprises a photoelectric converter disposed to receive irregularly reflected light of said exciting light beam in said measuring flow path.

5. A device for measuring the number of bacteria in superpure water, comprising:

means for conducting water under test including a measuring flow path;

means for adding a reagent to the water in said measuring flow path of a type such that products formed by reaction of said reagent with bacteria fluoresce when exposed to an exciting light beam;

an exciting light source for applying an exciting light beam to said water in said measuring flow path to cause said reaction products to fluoresce;

a photoelectric converter receiving light produced when said products fluoresce; and a spherical mirror positioned to reflect with high efficiency fluorescent light produced by applying said exciting light beam to said water in said flow path to said photoelectric converter, said measuring flow path being rectangular in section and having a small thickness in a direction of application of said exciting light beam and a large width perpendicular to a direction of said thickness, said exciting light beam being linearly applied in a widthwise direction of said measuring flow path.

6. The device as claimed in claim 5, wherein said exciting light source comprises a laser source and a plurality of cylindrical lenses, said exciting light beam being applied linearly in said widthwise direction of said measuring flow path through said cylindrical lenses.

7. The device as claimed in claim 5, wherein said reagent comprises at least one reagent selected from the group consisting of fluorescein diacetate, ethidium bromide, and ethidium iodide.

8. The device as claimed in claim 5, wherein said device further comprises a photoelectric converter disposed to receive irregularly reflected light of said exciting light beam in said measuring flow path.

* * * * *